United States Patent
Wu et al.

(10) Patent No.: US 7,521,452 B2
(45) Date of Patent: Apr. 21, 2009

(54) PREPARATION OF PHARMACEUTICAL SALTS OF PIPERAZINE COMPOUNDS

(75) Inventors: Wenxue Wu, Princeton Junction, NJ (US); Loc Thanh Tran, Parsippany, NJ (US); Bosco D'Sa, Edison, NJ (US); Feng Liang, Monmouth Junction, NJ (US); William Leong, Westfield, NJ (US); Hong-Chang Lee, Livingston, NJ (US); Kevin Klopfer, Flemington, NJ (US); Vijay Sabesen, Millbrae, CA (US)

(73) Assignee: Schering Corporation, Kenilworth, NJ (US)

( * ) Notice: Subject to any disclaimer, the term of this patent is extended or adjusted under 35 U.S.C. 154(b) by 89 days.

(21) Appl. No.: 11/326,155

(22) Filed: Jan. 5, 2006

(65) Prior Publication Data

US 2006/0241295 A1 Oct. 26, 2006

Related U.S. Application Data

(60) Provisional application No. 60/641,910, filed on Jan. 6, 2005.

(51) Int. Cl.
*A61K 31/497* (2006.01)
*C07D 239/02* (2006.01)
(52) U.S. Cl. .................. 514/252.18; 544/335
(58) Field of Classification Search ................ 544/335; 514/252.18
See application file for complete search history.

(56) References Cited

U.S. PATENT DOCUMENTS 6,720,325 B2 * 4/2004 Miller .................. 514/252.18
6,724,325 B2    4/2004 Fox

FOREIGN PATENT DOCUMENTS

| WO | WO00/66558 | 11/2000 |
| WO | WO02/079194 A1 | 10/2002 |
| WO | WO03/048153 A1 | 6/2003 |
| WO | WO03/066593 A2 | 8/2003 |

OTHER PUBLICATIONS

International Search Report for PCT/US2006/000261; mailed Jul. 6, 2006.

* cited by examiner

*Primary Examiner*—James O. Wilson
*Assistant Examiner*—Erich A Leeser
(74) *Attorney, Agent, or Firm*—Patent Practitioners of Schering Corporation

(57) ABSTRACT

The present invention is generally directed to a process to directly prepare pharmaceutically acceptable salts enriched with respect to selected rotameric salts of a basic compound, by creative choice of an acid and a solvent medium. The process is particularly useful in preparing specific rotamers of pharmaceutically useful salts in desired preponderance of a rotamer.

9 Claims, No Drawings

PREPARATION OF PHARMACEUTICAL SALTS OF PIPERAZINE COMPOUNDS

CROSS REFERENCE TO PRIORITY APPLICATION

This application claims the benefit of priority from U.S. provisional patent application Ser. No. 60/641,910 filed Jan. 6, 2005.

FIELD OF THE INVENTION

This patent application generally discloses a novel process to prepare pharmaceutically useful salts. It specifically discloses a novel process to synthesize pharmaceutically useful salts of piperazine compounds such as piperazine, 4-[4-[(R)-[1-[(cyclopropylsulfonyl)-4-piperidinyl](3-fluorophenyl)methyl]-3(S)-methyl-1-piperazinyl]-1-[(4,6-dimethyl-5-pyrimidinyl)carbonyl]-4-methylpiperidine (Formula 1). It further discloses a process to prepare pharmaceutical salts that are enriched in desired specific rotameric configurations.

BACKGROUND OF THE INVENTION

4-[4-[(R)-[1-[(Cyclopropylsulfonyl)-4-piperidinyl](3-fluorophenyl)methyl]-3(S)-methyl-1-piperazinyl]-1-[(4,6-dimethyl-5-pyrimidinyl)carbonyl]-4-methylpiperidine (Formula 1 ) is disclosed U.S. Pat. No. 6,720,325 to Miller, incorporated herein by reference.

U.S. Pat. No. 6,720,325 discloses several novel antagonists of the CCR5 receptor which are useful for the treatment of AIDS and related HIV infections, including the compound of Formula 1. CCR5 receptors have also been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

Generally, pharmaceutical compounds are used as their pharmaceutically acceptable salts. This is true of CCR5 receptor antagonists such as the compound of Formula 1 too, which makes the preparation of pharmaceutically acceptable salts of such compounds quite important.

The compound of Formula 1 has two chiral centers and the absolute configurations of the chiral centers are controlled by the chemical synthesis. However, the compound of Formula 1 exists as a mixture of rotational isomers or rotamers. There are two rotamers (diastereomeric—relationship between the two) resulting from restricted rotation about the amide bond marked "a" in FIG. 1 and in Scheme 1. For present purposes, enantiomers of rotamer 1 are considered inclusively as rotamer 1 and the enantiomers of rotamer 2 are considered inclusively as rotamer 2 which will be apparent from the examples that follow. The two rotamers may be denoted as rotamers 1 and 2, in order of their elution from a HPLC column, rotamer 1 being the one eluting first, and rotamer 2 eluting second.

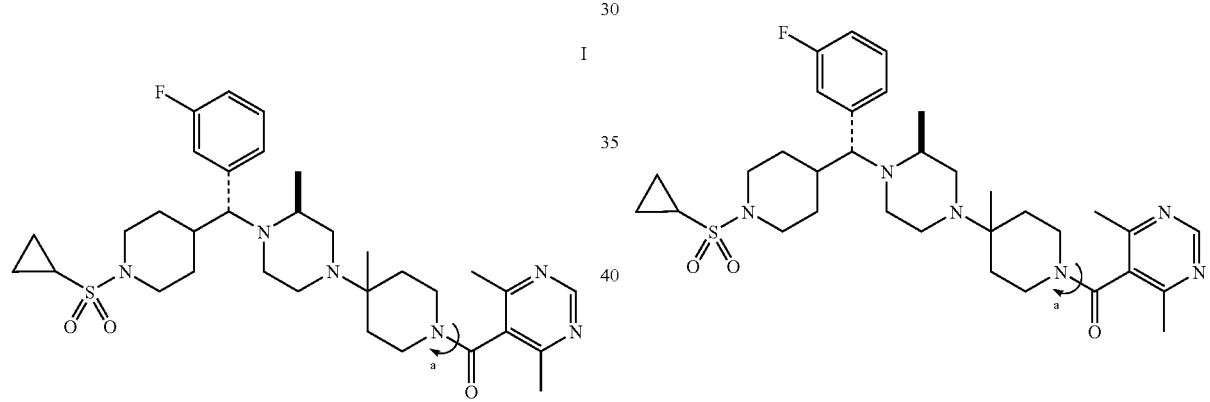

FIG. 1

Scheme 1 illustrates rotation about the amide bond for two example rotamers:

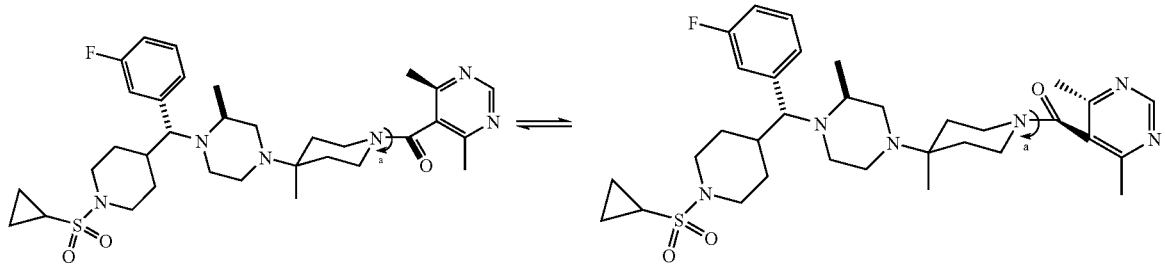

Scheme 1

While general synthetic approaches for salts typically yield a 1:1 ratio of the rotamers 1 and 2, it would be preferable to find methods of synthesis that would yield rotamer populations that are enriched in certain rotamers preferentially.

Pending U.S. application, Ser. No. 10/305,100 filed Nov. 26, 2002 describes the preparation of the pharmaceutical salts of bipiperidine compounds wherein the process results in the formation of certain enriched rotamer populations.

It would be preferable to find methods of synthesis for piperazine compounds that would yield rotamer populations that are enriched in certain rotamers preferentially. In view of the fact that the rotational barrier in amides is rather small, the period of rotation is consequently short and rapid interconversion takes place (see, for example, "*Comprehensive Organic Chemistry*", Vol. 2, ed. I. O. Sutherland, Pergamon Press, New York, 1979, pages 987-988), novel methods are needed to achieve the desired preferentially enriched rotamer population.

SUMMARY OF THE INVENTION

In an embodiment, the present invention discloses a process for preparing a mixture of rotamers of a salt of a basic compound, for example a substituted piperazine compound, wherein said mixture comprises one or more rotamers of the salt in a higher (i.e., preferentially enriched) molar percent than other corresponding rotamer(s) of the salt, with the process comprising reacting said basic compound with an acid in admixture with a solvent. The invention also teaches a method for preparing pharmaceutically useful salts. Additionally, it teaches a method for the formation of the salts, pharmaceutically useful or otherwise, of the compound of Formula 1 in high yields. It also teaches the direct preparation of specific rotamers of a salt of the compound of Formula 1 in high yields and in higher molar percent than other corresponding rotamers of the salt. In doing so, the process maintains the stereochemistry in the compound of Formula 1 undisturbed. In addition, it enables the formation of a mixture of rotamers of a salt of a basic compound wherein said mixture comprises one or more rotamers of the salt in a higher molar percent than other corresponding rotamers of the salt, with the salt being prepared by a process comprising reacting said basic compound with an acid in admixture with a solvent.

The term "high yields" refers to more than about 50% yield of the desired enriched product. Thus, unlike previously known processes which result in a 1:1 ratio of the salts of the rotamers 1 and 2, the present process offers a way to obtain the selective formation of unequal ratios of the salts of the desired rotamer directly. The term "higher molar percent" refers to selective preferred formation of a certain rotamer (or diastereoisomer) or rotamers over the other corresponding rotamer (or diastereoisomer) or rotamers by at least about a 55:45 ratio of molar percent. The formation of such differential ratio of rotamer (or diastereoisomer) directly in the present process is influenced by the unique choice of the solvent medium for the reaction between the particular acid and the basic compound. The term 'directly' means 'without the need for an additional step to separate the 50:50 rotamers obtained', for example, in the conventional processes. Thus, for example, if rotamer 2 is the desired one with high pharmaceutical activity, the present process makes it possible to obtain that rotamer directly instead of having to make an equimolar mixture of the rotamers 1 and 2 by previously known processes, followed by cumbersome separation of the mixture; such a separation may or may not yield the desired salt in decent yields and the process is also likely to be expensive.

Since the activity of pharmaceutical compositions may differ depending upon the type of salt they are comprised of, the present process affords a unique way to obtain desired specific salts with good pharmaceutical activity in highly enriched rotameric content. In the case of the compound of Formula 1, the present process achieves such preferential formation of the isomers by creative selection of the acid (for salt formation) and solvent medium for the salt-forming reaction.

The inventive process to make differing ratio of the rotamers of the salts of the compound of Formula 1 has several advantages: it is economical, can be easily scaled-up, affords the desired, preferentially enriched rotamer ratio in high yields and is generically applicable.

DESCRIPTION OF THE INVENTION

In one embodiment, the present invention discloses a novel, easy-to-use process for preparing a pharmaceutical salt of the compound of Formula 1 in high yields. It also teaches the preferential preparation of specific rotamers of the salt of the compound of Formula 1 in high yields. The present process comprises generally reacting the compound of Formula 1 (or a similar base) with an acid in admixture with a selected solvent medium in order to obtain differing ratios of rotamers as salts. The term "admixture" refers to physical contact of the ingredients as is known to those skilled in the art such as, for example, solution, suspension, emulsion, contact through a matrix such as, running through a column, and the like. In an illustration, as shown in one of the following EXAMPLES, the ratio of the 1:2 pair in the solid benzenesulfonate salt of the compound of Formula 1 is respectively 1:99 when prepared in acetone. However, that ratio changes to 7:93 when prepared in EtOH/MTBE. Other salts may be prepared similarly by changing the acid and the solvent as shown later.

In another embodiment, the present invention is directed to the process herein wherein said molar percent of said one or more rotamers of the salt to said other corresponding rotamer or rotamers of the salt is 45:55.

In another embodiment, the present invention directed to the process herein wherein said molar percent of said one or more rotamers of the salt to said other corresponding rotamer or rotamers of the salt is 25:75.

In another embodiment, the present invention directed to the process herein wherein said molar percent of said one or more rotamers of the salt to said other corresponding rotamer or rotamers of the salt is at least about 10:90.

In another embodiment, the present invention directed to the process herein wherein said molar percent of said one or more rotamers of the salt to said other corresponding rotamer or rotamers of the salt is 5:95.

In another embodiment, the present invention directed to the process herein wherein one rotamer is present in an amount greater than about 55 molar percent of the total amount of salt present.

In another embodiment, the present invention directed to the process herein wherein one rotamer is present in an amount greater than about 75 molar percent of the total amount of salt present.

In another embodiment, the present invention is directed to the process herein wherein one rotamer is present in an amount greater than about 90 molar percent of the total amount of salt present.

In another embodiment, the present invention is directed to the process herein wherein one rotamer is present in an amount greater than about 95 molar percent of the total amount of salt present.

In another embodiment, the present invention is directed to the process herein wherein said substituted piperazinyl compound is a pharmaceutical compound.

In another embodiment, the present invention is directed to the process herein wherein said acid is a pharmaceutically useful acid.

In another embodiment, the present invention is directed to the process herein wherein said acid is used in a ratio from about 1:1 to about 3:1 with respect to said substituted piperazinyl compound.

In another embodiment, the present invention is directed to the process herein wherein said solvent is used in a ratio from about 5:1 to about 20:1 with respect to said substituted piperazinyl compound.

In another aspect, the present invention is directed to a process wherein said substituted piperazinyl compound has the structure of Formula 1:

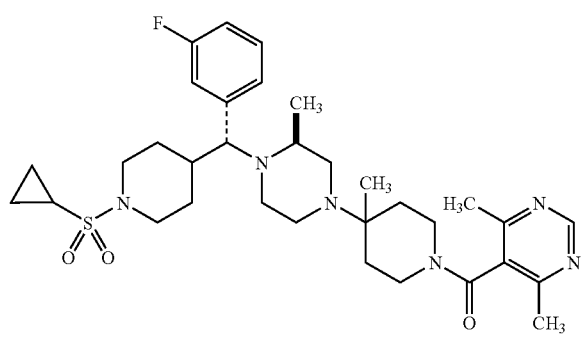

Formula I

In still another aspect, the present invention is directed to a process wherein said higher molar percent refers to the concentration of rotamer 1 of the salt of said compound of Formula 1 compared to the rotamer 2 of the salt of said compound of Formula 1.

In still another aspect, the present invention is directed to a process wherein said higher molar percent refers to the concentration of the rotamer 2 of the salt of said compound of Formula 1 compared to the rotamer 1 of the salt of said compound of Formula 1.

In another embodiment, the present invention is directed to the process herein wherein said salt is selected from the group consisting of benzenesulfonate, nicotinate, benzoate, hydrochloride salt, glutarate, D-10-camphorsulfonate and 2-ketoglutarate.

In still another embodiment, the present invention is directed to the process herein wherein said salt is benzenesulfonate.

In yet another embodiment, the present invention is directed to the process herein wherein said benzenesulfonate is prepared by reacting the compound of Formula 1 with benzenesulfonic acid in a solvent.

In still yet another embodiment, the present invention is directed to the process herein wherein said benzenesulfonate is formed at about 0-80° C.

In still yet another embodiment, the present invention is directed to the process herein wherein said salt is D-10-camphorsulfonate.

In another embodiment, the present invention is directed to the process herein wherein said D-10-camphorsulfonate is prepared by reacting the compound of Formula 1 with D-10-camphorsulfonic acid in an ester solvent.

In yet another embodiment, the present invention is directed to the process herein wherein said D-10-camphorsulfonate is prepared by reacting the compound of Formula 1 with D-10-camphorsulfonic acid in ethyl acetate.

In still another embodiment, the present invention is directed to the process herein wherein said salt is glutarate.

In still yet another embodiment, the present invention is directed to the process herein wherein said glutarate is prepared by reacting said compound of Formula 1 with glutaric acid in a nitrile solvent.

In another embodiment, the present invention is directed to the process herein wherein said nitrile is acetonitrile.

In still another embodiment, the present invention is directed to the process herein wherein said salt is 2-ketoglutarate.

In yet another embodiment, the present invention is directed to the process herein wherein said 2-ketoglutarate is prepared by reacting said compound of Formula 1 with 2-ketoglutaric acid in a nitrile solvent.

In still yet another embodiment, the present invention is directed to the process herein wherein said nitrile is acetonitrile.

In another embodiment, the present invention is directed to the process herein wherein said salt is a nicotinate.

In still another embodiment, the present invention is directed to the process herein wherein said nicotinate is prepared by reacting said compound of Formula 1 with nicotinic acid in water.

In yet another embodiment, the present invention is directed to the process herein wherein said salt is benzoate.

In still yet another embodiment, the present invention is directed to the process herein wherein said benzoate is prepared by reacting said compound of Formula 1 with benzoic acid in a mixture of water and acetone solvent.

In another embodiment, the present invention is directed to the process herein wherein said solvent is water, a ketone, ether, ester, alcohol, nitrile, hydrocarbon or mixtures thereof.

In another embodiment, the present invention is directed to the process herein wherein said ester solvent is selected from the group consisting of ethyl acetate, isopropyl acetate and mixtures thereof.

In another embodiment, the present invention is directed to the process herein wherein said alcohol solvent is selected from the group consisting of methyl alcohol, ethyl alcohol, isopropyl alcohol and mixtures thereof, said nitrile is acetonitrile, and said ether is tetrahydrofuran ("THF"), and said hydrocarbon is toluene.

In another aspect, the present invention is directed to a process for preparing a mixture of rotamers of the benzenesulfonate salt of a compound of Formula 1, wherein said mixture comprises one or more rotamers of the benzenesulfonate salt in a higher molar percent than other corresponding rotamer or rotamers of the benzenesulfonate salt, said process comprising:

(a) preparing a first intimate mixture of said compound of Formula 1 in a solvent;

(b) maintaining said first intimate mixture at about 0-10° C.;

(c) preparing a second intimate mixture of benzene sulfonic acid in the same or different solvent as stated in step (a);

(d) combining said first intimate mixture and said second intimate mixture at 0-10° C. to prepare a combined mixture and heating the combined mixture to induce crystallization of the benzenesulfonate salt; and (e) isolating the benzenesulfonate salt.

In another aspect, the present invention is directed to such process wherein said molar percent of said one rotamer of the benzenesulfonate salt to said the other corresponding rotamer of the benzenesulfonate salt is 45:55.

In still another aspect, the present invention is directed to such process wherein said molar percent of said one rotamer of the benzenesulfonate salt to said other corresponding rotamer of the benzenesulfonate salt is 25:75.

In yet another aspect, the present invention is directed to such process wherein said molar percent of said one rotamer of the benzenesulfonate salt to said other corresponding rotamer of the benzenesulfonate salt is 10:90.

In still yet another aspect, the present invention is directed to such process wherein said molar percent of said one rotamer of the benzenesulfonate salt to said other corresponding rotamer of the benzenesulfonate salt is 5:95.

In another aspect, the present invention is directed to such process wherein said solvent is water, a ketone, ether, ester, alcohol, nitrile, hydrocarbon or mixtures thereof.

In another aspect, the present invention is directed to such process wherein said ester solvent is selected from the group consisting of ethyl acetate, isopropyl acetate and mixtures thereof.

In still another aspect, the present invention is directed to such process wherein said ester solvent is isopropyl acetate.

In yet another aspect, the present invention is directed to such process wherein said ketone solvent is acetone.

In yet still another aspect, the present invention is directed to such process wherein said ether solvent is THF.

In another embodiment, the present invention is directed to such process wherein said nitrile solvent is acetonitrile.

In still another embodiment, the present invention is directed to such process wherein said hydrocarbon solvent is toluene.

In yet another embodiment, the present invention is directed to such process wherein said alcohol solvent is selected from the group consisting of methyl alcohol, ethyl alcohol, isopropyl alcohol and mixtures thereof.

In still yet another embodiment, the present invention is directed to such process wherein said alcohol solvent is ethyl alcohol.

In another embodiment, the present invention is directed to such process wherein said solvent comprises isopropyl acetate and ethyl alcohol.

In another aspect, the present invention is directed to a mixture of rotamers of a salt of a substituted piperazinyl compound wherein said mixture comprises one or more rotamers of the salt in a higher molar percent than other corresponding is rotamer or rotamers of the salt. Said salt can be prepared by a process comprising reacting said substituted piperazinyl compound with an acid in admixture with a solvent. Here again the solvents may be water, a ketone, ether, ester, alcohol, nitrile, hydrocarbon or mixtures thereof.

In still another aspect, the present invention is directed to a mixture wherein said substituted piperazinyl compound is the compound of Formula 1:

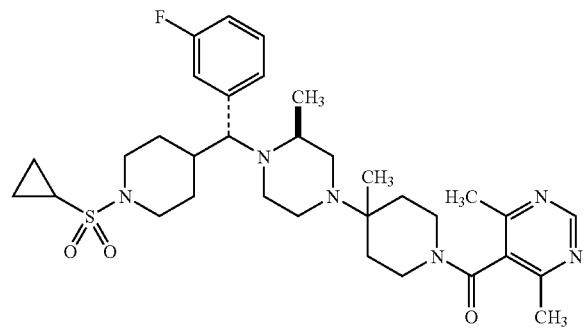

Formula I said acid is benzenesulfonic acid, said salt is benzenesulfonate, and said molar percent is 45:55 of one rotamer of the benzenesulfonate salt to said other corresponding rotamer of the benzenesulfonate salt. Solvents may be as noted above.

The salts in the mixture can be selected from the group consisting of acetate, benzenesulfonate, benzoate, bicarbonate, bromide, calcium edetate, camphorsulfonate, carbonate, chloride/dihydrochloride, citrate, N,N-di(dehydroabietyl)ethylenediamine, edetate, 1,2-ethanedisulfonate, ethanesulfonate, fumarate, glucoheptonate, gluconate, glutamate, glutarate, 2-ketoglutarate, p-glycollamidophenylarsonate, hexylresorcinate, hyclate, hydrobromide, hydrochloride, 2-hydroxyethanesulfonate, hydroxynaphthoate, iodide, lactate, lactobionate, lauryl sulfonate, malate, maleate, mandelate, methanesulfonate, methylbromide, methylnitrate, methylsulfate, mucate, nafate, napsylate, nitrate, pamoate, pantothenate, phosphate/diphosphate, polygalacturonate, salicyclate, sodium succinate, stearate, subacetate, succinate, sulfate, tosylate, tannate, tartarate/bitartarate, 8-chlorotheophyllinate, triethiodide, adipate, alginate, aminosalicyclate, anhydromethylenecitrate, arecoline, asparate, bisulfate, butylbromide, camphorate, digluconate, dihydrobromide, disuccinate, glycerophosphate, hemisulfate, hydrofluoride, hydroiodide, methylenebis(salicyclate), naphthalenedisulfonate, oxalate, pectinate, persulfate, phenylethylbarbiturate, picrate, propionate, thiocyanate, undecanoate, acetylaminoacetate, N-acetyl-L-asparaginate, N-acetylcystinate, adamantoate, adipoate, N-alkylsulfamates, anthraquinone-1,5-disulfonate, arabolactansulfate, argininate, aspartate, betaine, carnitine, 4-chloro-m-toluenesulfonate, decanoate, diacetyl sulfate, dibenzylethylenediamine, dimethylamine, diguaiacylphosphate, dioctylsulfosuccinate, pamoate, fructose-1,6-diphosphate, glucose phosphate, L-glutaminate, hydroxynaphthoate, lauryl sulfate, lysine, 2-naphthalenesulfonate, octanonate, tannate and theobromine acetate.

In specific embodiment, the present invention is directed to a benzenesulfonate salt of a substituted piperazinyl compound, wherein said substituted piperazinyl compound has the formula:

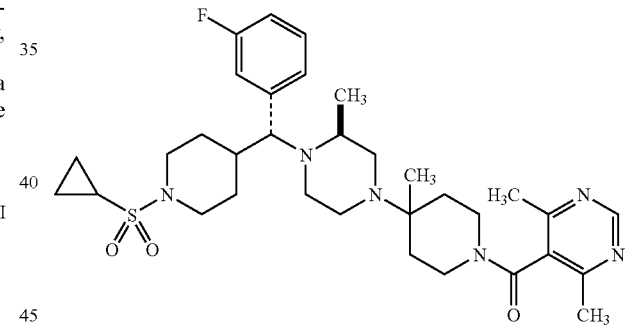

In another specific embodiment, the present invention is directed to a D-10-camphorsulfonate salt of a substituted piperazinyl compound, wherein said substituted piperazinyl compound has the formula:

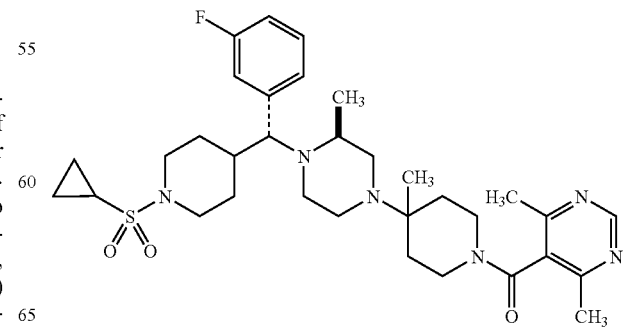

In still another embodiment, the present invention is directed to a glutarate salt of a substituted piperazinyl compound, wherein said substituted piperazinyl compound has the formula:

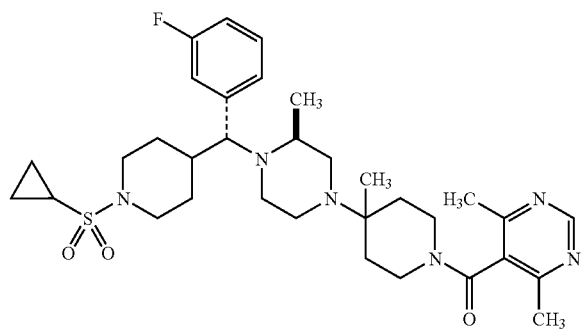

In yet another specific embodiment, the present invention is directed to a 2-ketoglutarate salt of a substituted piperazinyl compound, wherein said substituted piperazinyl compound has the formula:

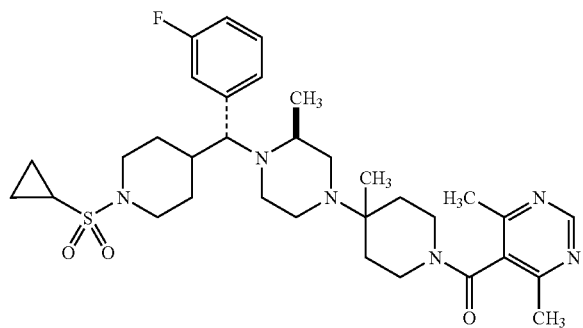

In still yet another specific embodiment, the present invention includes a nicotinate salt of a substituted piperazinyl compound, wherein said substituted piperazinyl compound has the formula:

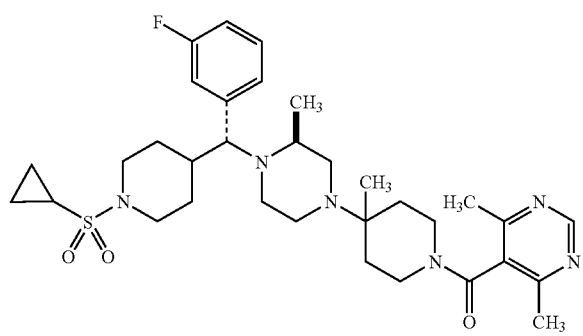

In yet still another specific embodiment, the present invention is directed to a benzoate salt of a substituted piperazinyl compound, wherein said substituted piperazinyl compound has the formula:

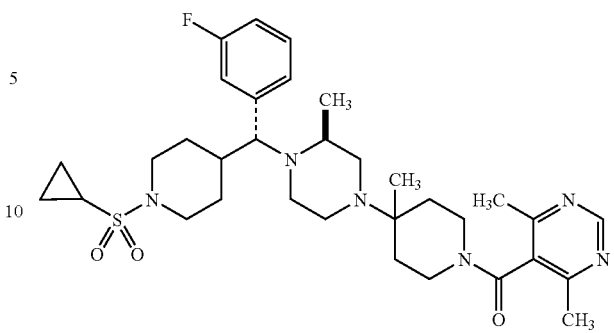

In addition, the present invention includes a hydrochloride salt of a substituted piperazinyl compound, wherein said substituted piperazinyl compound has the formula:

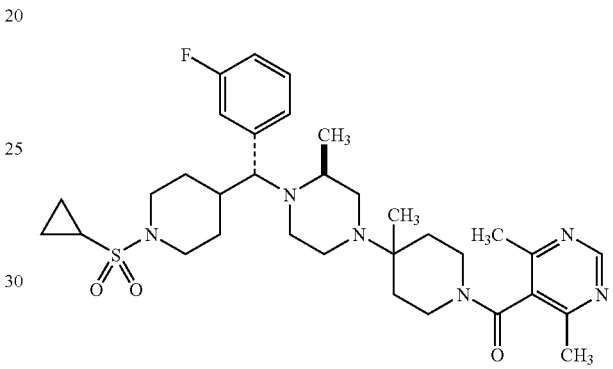

Furthermore, the present invention is directed to a process for selectively crystallizing a rotamer of a salt of a compound of Formula 1:

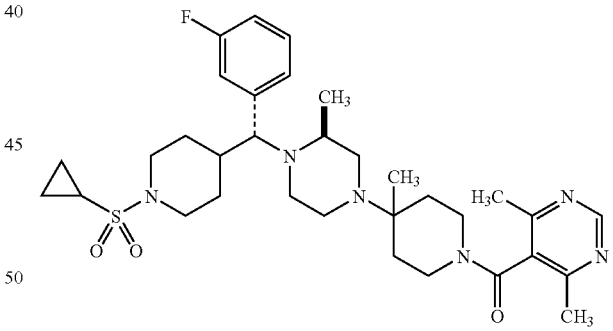

said process comprising reacting said compound of Formula 1 with an acid in admixture with a solvent.

The processes, while described and illustrated herein as the preparation of specific desired rotamers of the compound of Formula 1, are applicable generically to the preparation of pharmaceutically useful salts from basic pharmaceutical compositions. By appropriate choice of the solvent medium, the reaction of the basic compound with an acid (from which the salt is to be derived) to form the salt selectively yields the desired rotameric compositions in enriched molar percent. Thus, in another embodiment, the invention offers a novel, simple process to directly prepare desired salts of basic compounds in unequal ratios of rotamers or rotameric pairs. In yet another embodiment, the present invention teaches the formation of pharmaceutically useful salts in high yields and selectivity of rotamer population.

The following non-limiting list includes anions representing suitable acids which may be used to form salts in accordance with the present invention. The list of anions for useful salts includes, for example, acetate, benzenesulfonate, benzoate, bicarbonate, bromide, calcium edetate, camphorsulfonate, carbonate, chloride/dihydrochloride, citrate, N,N-di(dehydroabietyl)ethylenediamine, edetate, 1,2-ethanedisulfonate, ethanesulfonate, fumarate, glucoheptonate, gluconate, glutamate, p-glycollamidophenylarsonate, hexylresorcinate, hyclate, hydrobromide, hydrochloride, 2-hydroxyethanesulfonate, hydroxynaphthoate, iodide, lactate, lactobionate, lauryl sulfonate, malate, maleate, mandelate, methanesulfonate, methylbromide, methylnitrate, methylsulfate, mucate, nafate, napsylate, nitrate, pamoate, pantothenate, phosphate/diphosphate, polygalacturonate, salicyclate, sodium succinate, stearate, subacetate, succinate, sulfate, tosylate, tannate, tartrate/bitartarte, 8-chlorotheophyllinate, triethiodide, adipate, alginate, aminosalicyclate, anhydromethylenecitrate, arecoline, asparate, bisulfate, butylbromide, camphorate, digluconate, dihydrobromide, disuccinate, glycerophosphate, hemisulfate, hydrofluoride, hydroiodide, methylenebis(salicyclate), naphthalenedisulfonate, oxalate, pectinate, persulfate, phenylethylbarbiturate, picrate, propionate, thiocyanate, undecanoate, acetylaminoacetate, N-acetyl-L-asparaginate, N-acetylcystinate, adamantoate, adipoate, N-alkylsulfamates, anthraquinone-1,5-disulfonate, arabolactansulfate, argininate, aspartate, betaine, carnitine, 4-chloro-m-toluene-sulfonate, decanoate, diacetyl sulfate, dibenzylethylenediamine, dimethylamine, diguaiacylphosphate, dioctylsulfosuccinate, pamoate, fructose-1,6-diphosphate, glucose phosphate, L-glutaminate, hydroxynaphthoate, lauryl sulfate, lysine, 2-naphthenesulfonate, octanonate, tannate and theobromine acetate. Additionally, acids which are generally considered suitable for the formation of pharmaceutically useful salts from basic pharmaceutical compounds are discussed, for example, by S. Berge et al, *Journal of Pharmaceutical Sciences* (1977) 66(1),1-19; P. Gould, *International J. of Pharmaceutics* (1986) 33 201-217; Anderson et al, "*The Practice of Medicinal Chemistry*" (1996), Academic Press, New York; Stahl, et al, "*Handbook of Pharmaceutical Salts: Properties, Selection and Use*" (2002), Wiley-VCH, Zurich; and in *The Orange Book* (Food & Drug Administration, Washington, D.C. on their website). These disclosures are incorporated herein by reference.

In general, known processes to form salts by reaction of basic compounds with acids yields equal ratios of rotamers or rotameric pairs, which need to be later separated in yet another step. The present process, which avoids such separation by preferentially enriching in certain rotamer populations during the salt formation reaction itself, is superior.

The present process may be illustrated by the formation of the benzenesulfonate salt of the compound of Formula 1. The compound of Formula 1, which is basic, may be dissolved or otherwise intimately mixed or suspended in a suitable solvent medium. Non-limiting examples of suitable solvent media are, for example, water, ketone, ether, ester, alcohol, nitrile, hydrocarbon or mixtures thereof. Non-limiting examples of suitable ketones include, for example, acetone, methyl ethyl ketone, methyl n-amyl ketone and the like and mixtures thereof, preferably acetone. Non-limiting examples of suitable ethers are, for example, tetrahydrofuran, diglyme, methyl ethyl ether and mixtures thereof, preferably tetrahydrofuran. Non-limiting examples of suitable esters are, for example, ethyl acetate, isopropyl acetate and mixtures thereof. Non-limiting examples of suitable alcohols are, for example, methyl alcohol, ethyl alcohol, isopropyl alcohol and mixtures thereof. Non-limiting examples of suitable nitriles are, for example, acetonitrile, propionitrile and mixtures thereof. Non-limiting examples of suitable hydrocarbons are, for example toluene, xylene, chlorobenzene, hexane, heptane and mixtures thereof, preferably toluene. Benzene sulfonic acid may be added to this either as solid or as a solution (or intimate mixture or suspension) in the same solvent. The acid is used generally in 3:1 mole ratio, preferably in a 1.5:1 molar ratio and typically in 1:1 molar ratio, with respect to the compound of Formula 1. The total quantity of the solvent may be about a 20:1 ratio, preferably about a 18:1 ratio and typically about a 15:1 ratio, with respect to the compound of Formula 1. The mixture is stirred or mixed otherwise, generally at about 0-80° C., preferably at about 0-40° C. and typically at about 0-10° C. for about 1-15 hours, and then kept at 0-80° C., preferably at 40-80° C., and typically at about 80° C. to allow the completion of crystal formation of the salt. Upon cooling, the salt may be isolated by filtration or such similar methods. When isopropyl acetate was used as the solvent in an Example, a rotamer ratio of 1:99 (for the 1:2 isomer pair) was found in the benzenesulfonate salt so formed.

If the compound of Formula 1 is dissolved in an ether solvent such as tetrahydrofuran and treated with benzene sulfonic acid as a solid or as dissolved (or mixed or suspended) in tetrahydrofuran in the process noted above, a rotamer ratio of 2:98 of the above-noted isomer pairs is obtained.

Yet another example is the preparation of the camphorsulfonate salt of the compound of Formula 1. If the camphorsulfonate salt is prepared from the compound of Formula 1 and camphor sulfonic acid in an alcohol/ester solvent for example, a rotamer ratio of 98:2 is obtained for the 1:2 isomer pair. If, however, the solvent is changed to an ester, for example, the same ratio changes to 96:4 in the salt obtained.

The salts prepared by the present invention exhibit desirable physical and chemical characteristics suitable for pharmaceutical uses. Non-limiting examples of such characteristics include physical stability, chemical stability, thermal stability, desirable hygroscopicity, solubility, fluidity and the like.

The following nonlimiting EXAMPLES and TABLE 1 are provided in order to further illustrate the present invention.

EXAMPLES

In the following Examples and Table 1, ratios are given as rotamer 1:rotamer 2 wherein rotamer 1 is the first to elute and rotamer 2 is the second to elute from a HPLC column. For example, in Example 1 below wherein the rotamer ratio is 1:99 by HPLC, rotamer 1 was present in 1 part to 99 parts of rotamer 2. Herein mole ratio equals w/w since the molecular weights of the rotamers are equal. Unless otherwise stated, the following abbreviations have the stated meanings in the Examples and Table 1 below:

ACN=Acetonitrile
$CDCl_3$=Deuterated chloroform
$D_2O$=Deuterium Oxide (heavy water)
DMSO=dimethylsulfoxide
DSC=Differential Scanning Calorimetry
EtOAc=Ethyl acetate
EtOH=Ethanol
g=grams
HPLC=High Performance Liquid Chromatography
IPA=Isopropyl alcohol
iPrOAc or IPOAc=Isopropyl acetate K₂HPO₄=Potassium Hydrogen Phosphate
M.p.: melting point
MeOH=Methanol
MHz=Megahertz
mL=milliliters
MTBE=Methyl t-butyl ether
NMR=nuclear magnetic resonance spectroscopy
THF=Tetrahydrofuran Example 1

Preparation of the Benzenesulfonic Acid salt of the Compound of Formula 1 (1:99)

A solution of amine compound of Formula 1 in isopropyl acetate (350 mL, 100 g active, 159 mmol) was diluted with ethanol (300 mL). To this solution was added benzenesulfonic acid (26.5 g, 1.05 eq) dissolved in isopropyl acetate (300 mL) at 0-10° C. The reaction mixture was heated at reflux for 3 hours and cooled slowly to room temperature. After a 2 hour hold, the slurry was filtered and the solids were washed 30% ethanol/isopropyl acetate and dried under vacuum. The isolated yield was 85%. The rotamer ratio was 1:99 by HPLC. m.p.: 257.7° C. (dec., DSC onset). $^1$H NMR (400 MHz, CDCl₃, mixture of rotamers) δ 10.66 (br, s, 1H), 8.91 (s, 1H), 7.53 (m, 2H), 7.29 (m, 4H), 6.95 (t, J=8.2 Hz, 1H), 6.89 (d, J=7.5 Hz, 1H), 6.82 (d, J=9.2 Hz, 1H), 4.93 (br d, J=13.2 Hz, 1H), 3.84 (d, J=10.5 Hz, 1H), 3.64 (m, 2.5H), 3.53 (d, J=10.6 Hz, 0.5H), 3.41 (t, J=13.1 Hz,1H), 3.32 (d, J=11.2 Hz, 0.5H), 3.22 (d, J=10.2 Hz, 0.5H), 2.62-3.15 (m, 8H), 2.55 (br m, 1H), 2.41 (s, 1.5H), 2.40 (s, 1.5H), 2.37 (m, 1.5H), 2.35 (s, 3H), 2.20 (m, 1.5H), 2.21 (br m, 1H), 1.95 (br m, 2H), 1.75 (Br S, 1H)1.49 (s, 3H), 1.10-1.48 (m, 8.5H), 0.95 (m, 2.5H); $^{13}$C NMR (MHz, CDCl₃, −10° C., mixture of diastereomers) δ 165.97, 165.87, 163.85, 163.74, 163.50, 162.20, 162.15, 161.54, 157.71, 144.20, 136.85, 130.34, 130.00, 128.21, 128.13, 125.51, 124.51, 115.50, 115.32, 115.05, 114.88, 77.23, 65.34, 64.74, 64.71, 51.42, 51.35, 50.03, 46.25, 45.71, 42.20, 37.35, 37.31, 35.54, 35.46, 32.45, 32.31, 31.46, 31.26, 30.00, 29.80, 24.95, 24.89, 22.16, 21.97, 17.89, 15.01, 14.89, 4.27, 4.16; HRMS calcd for C₃₃H₄₈FN₆O₃S (protonated compound of Formula 1): 627.3493, found 627.3479.

Example 2

Preparation of the d-10-camphorsulfonic Acid Salt of the Compound of Formula 1 (98:2)

The solution of d-10-camphorsulfonic acid (12.4 g, 53 mmol) in ethyl acetate (68 mL) was slowly added to a solution of compound of Formula 1 (34.0 g, 1.02 eq) in ethyl acetate (136 mL). The resulting solution was warmed to 65° C. and held at this temperature overnight. The heterogeneous mixture was cooled slowly to 0° C. and filtered. The solids were washed with ethyl acetate and dried in a vacuum oven to give a white solid (38.2 g, 81% yield). The rotamer ratio was 98:2 by HPLC. m.p.: 260.6° C. (dec., DSC onset). $^1$H NMR (400 MHz, CDCl₃): δ 8.9 (s, 1H),7.3 (br s, 1H), 7.0 (m, 3H), 5.0 (br d, 1H), 4.0 (br d, 1H), 3.3-3.7 (m, 4H), 3.3 (brd, 1H), 3.1 (m, 1H),2.7-3.0 (m, 7H), 2-2.6 (m, 15H), 1.9 (m, 5H), 1.8 (m, 2H), 1.6 (m, 4H), 1.0-1.5 (m, 14H), 88 (s, 3H).

Example 3

Glutaric Acid Salt of the Compound of Formula 1(3:97)

Compound of Formula 1 (2.6 g, 4.2 mmol) and glutaric acid (0.51 g, 1 eq) were mixed in 2.5 mL acetonitrile. The mixture was heated at 75-80° C. for 2 hours. After cooled slowly to room temperature, it was stirred overnight. The resulting slurry was filtered, washed with acetonitrile, and dried under vacuum to give a white solid (2.2 g, 70% yield). m.p.: 106.8° C. (DSC onset). Rotamer ratio was 3:97 by HPLC.
$^1$H NMR (400 MHz, CDCl₃): δ 8.91 (s, 1H), 7.29 (dd, J₁=14.0 Hz, J₂=7.8 Hz, 1H), 6.97 (dt, J₁=8.4 Hz, J₂=1.9 Hz, 1H), 6.88 (d, J=7.5 Hz, 1 H), 6.80 (d, J=10.1 Hz, 1H), 3.94 (brd, J=14.1 Hz, 1H), 3.85 (brd, J=12.0 Hz, 1H), 3.68 (brd, J=12.3 Hz, 1H), 3.63 (d, J=10.4 Hz, 1H), 3.50 (m, 1H), 3.23 (m, 1H), 2.79 (m, 1H), 2.72 (m, 2H), 2.63 (d, J=10.5 Hz, 2H), 2.43 (s, 3H), 2.40 (t, J=6.9 Hz, 4H), 2.36 (s, 3H), 2.22 (m, 5H), 2.00 (m, 7H), 1.74 (br d, J=13.2 Hz, 1H), 1.20-1.48 (m, 5H), 1.12 (m, 6H), 0.94 (m, 5H).

Example 4

2-Ketoglutaric Acid Salt of the Compound of Formula 1 (5:95)

Compound of Formula 1 (40 g, 64 mmol) and 2-ketoglutaric acid (8.8 g, 1 eq) were mixed in 400 mL acetonitrile. The mixture was heated at 75-80° C. for 2 hours. After cooled slowly to room temperature, the resulting slurry was filtered, washed with acetonitrile, and dried under vacuum to give a white solid (43.5 g, 89% yield). m.p. by DSC 136.3° C. (DSC onset). Rotamer ratio: 5:95. $^1$H NMR (400 MHz, D₂O, mixture of rotamers) δ 8.73 (s, 1H), 7.26 (dd, J₁=14.0 Hz, J₂=7.2 Hz, 1 H), 6.96 (m, 3H), 4.45 (br d, J=12.3 Hz, 1H), 3.75 (d, J=10.5 Hz, 1H), 3.59 (d, J=11.1 Hz, 1H), 3.25 (m, 6H), 2.91 (m, 2H), 2.75 (m, 5H), 2.48 (t, J=6.5 Hz, 2H), 2.39 (m, 2H), 2.27 (m, 1H), 2.25 (s, 3H), 2.22 (s, 3H), 2.00 (m, 3H), 1.75 (d, J=12.5 Hz, 1H), 1.65 (m, 1H), 1.54 (m, 1H), 1.28 (s, 3H), 1.13 (d, J=5.8 Hz, 3H). 1.25 (m, 2H), 0.92 (m, 5H).

Example 5

Nicotinic Acid Salt Octahydrate of the Compound of Formula 1(99:1)

Compound of Formula 1 (50 g, 80 mmol) and 9.8 g nicotinic acid (1 eq) were mixed in 800 ml water. The mixture was concentrated on a rotary evaporator and filtered to remove a small amount of insolubles. The filtrate was diluted to 500 ml with water and heated at 60° C. for 5 hours. A slurry was formed during heating. After cooled slowly to room temperature, it was filtered and washed with water. After dried at room temperature under vacuum, a white solid was obtained (44.3 g, 74% yield). The rotamer ratio was 99:1. DSC peaks: 88° C. (loss of hydration), 113° C. (m.p.). $^1$H NMR (400 MHz, DMSO-d₆, mixture of rotamers) δ 9.01 (d, J=2.0 Hz, 1H), 8.88 (s, 1H), 8.72 (dd, J₁=6.9 Hz, J₂=2.0 Hz, 1H), 8.20 (dt, J₁=8.0 Hz, J₂=1.9 Hz, 1H), 7.48 (dd, J₁=8.0 Hz, J₂=4.9 Hz, 1H), 7.34 (q, J=7.3 Hz, 1H), 7.01 (m, 3H), 3.70 (m, 1H), 3.65 (br s, 17H), 3.62 (m, 2H), 3.41 (m, 2H), 3.06 (m, 1H), 2.60-2.90 (m, 5H), 2.56 (d, J=10.1 Hz, 1H), 2.49 (m, 1H), 2.28 (s, 3H), 2.17 (s, 3H), 2.13 (m, 3H), 2.00 (m, 1H), 1.90 (m, 2H), 1.74 (brd, J=13.8 Hz, 1H), 1.61 ( brd, J=14.1 Hz, 1H), 1.37 (m, 1H), 1.20 (m, 2H), 1.08 (m, 1H), 1.05 (d, J=5.9 Hz, 3H), 0.90 (m, 5H), 0.86 (s, 3H).

Example 6

Benzoic Acid Salt Hexahydrate of the Compound of Formula 1 (95:5)

The compound of Formula 1 (2.0 g, 3.2 mmol) and benzoic acid (0.39 g, 1.0 eq) were mixed in water (15 mL) and acetone (1.5 mL). The mixture was stirred at 50° C. for 1 hour and then cooled to 25° C. The solid was filtered and dried at 30° C. under vacuum to give a white solid (0.9 g, 38% yield). The rotamer ratio was 95:5 by HPLC. DSC peaks: 72° C. (loss of hydration), 144° C. (m.p.). $^1$H NMR (400 MHz, CDCl$_3$, mixture of rotamers) δ 8.91 (s, 1 H), 8.04 (d, J=7.2 Hz, 2H), 7.55 (d, J=7.0 Hz, 1H), 7.44 (m, 2H), 7.24 (m, 1H), 6.87 (m, 3H), 4.72 (br s, 1H), 3.95 (brs, 1H), 3.84 (d, J=11.1 Hz, 1H), 3.67 (d, J=11.1 Hz, 1H), 3.60 (d, J=10.6 Hz, 1H), 3.48 (br s, 1H), 3.21 (br s, 1H), 1.80-3.00 [m, 31H including 2.43 (s, 3H), 2.34 (s, 3H), and 2.50 (br s, 13H)], 1.74 (br s, 1H), 1.33 (m, 4H), 1.09 (m, 6H), 0.93 (s, 5H).

Example 7

Hydrochloric Acid Salt of the Compound of Formula 1 (50:50)

To a solution of the compound of Formula 1 (6.0 g, 9.6 mmol) in isopropyl acetate (30 mL) was added concentrated hydrochloric acid (0.9 mL, 1.1 eq). The resulting mixture was heated at 50° C. for 30 minutes. Upon cooling slowly to room temperature, it was filtered and dried under vacuum to give an off-white solid (4.0 g). This solid was then slurried in diethylketone (40 mL) and heated at 90° C. for 1 hour. Upon cooling slowly to room temperature, it was filtered, washed with diethylketone, and dried under vacuum to give a white solid (3.2 g, 50% yield). This solid (200 mg) was then slurried in acetone (1 mL) and the mixture was stirred at room temperature for 1 week. The solids were filtered and dried under vacuum. The rotamer ratio was about 50:50. m.p. by DSC: 205.4° C. (onset).

Determination of the Rotamer Ratio using HPLC: The rotamer ratio was determined by injection of a sample of salt dissolved in cold water/acetonitrile into an HPLC column (248 nm detector; column: Phenomenex Luna C18(2), 4.6× 150 mm, 3 micron; column temperature: 10° C.) using a mobile phase of 15:80:5 (acetonitrile):(50 mM K$_2$HPO$_4$, pH 2.0 with 25 mM beta-cyclodextrin):(THF) at a flow rate of 0.7 mL/minutes. For a typical benzenesulfonic acid salt, the rotamers 1 and 2 were found to have retention times of about 8.7 minutes and 9.5 minutes, respectively.

TABLE 1

Crystallization using various solvents or solvent mixtures

| Salt | Solvent (rotamer ratio in solids) | | | | | |
|---|---|---|---|---|---|---|
| 1. Benzene sulfonate | EtOAc (4:96) THF (2:98) EtOH/ EtOAc | IPOAc (1:99) MeOH/ EtOAc (1:99) EtOH/ MTBE | Acetone (1:99) MeOH/ IPOAc (2:98) EtOH/ heptane | IPA (2:98) MeOH/ toluene (2:98) EtOH/ THF | EtOH (2:98) MeOH/ THF (1:99) EtOH/ acetone | Toluene (1:99) MeOH/ IPA (1:99) IPA/ EtOAc |
| 2. Camphor sulfonate | IPOAc (96:4) | EtOH/ EtOAc (96:4) | EtOH IPOAc (98:2) | | | |
| 3. Glutarate | EtOAc (5:95) | | | | | |
| 4. 2-Keto glutarate | EtOAc (5:95) | IPOAc (5:95) | Acetone (5:95) | IPA (5:95) | THF (5:95) | |
| 5. Hydro chloride | ACN (50:50) | Diethyl ketone (50:50) | | | | |

While the EXAMPLES and TABLE 1 are described herein as the preparation of the diastereomeric pairs of the salt of the compound of Formula 1, it will be apparent to those skilled in the art that many modifications, variations and alterations to the present disclosure, both to materials, methods and reaction conditions, may be practiced. All such modifications, variations and alterations are intended to be within the spirit and scope of the present invention.

What is claimed is:

1. A mixture of rotamers of a salt of a substituted piperazinyl compound of Formula I:

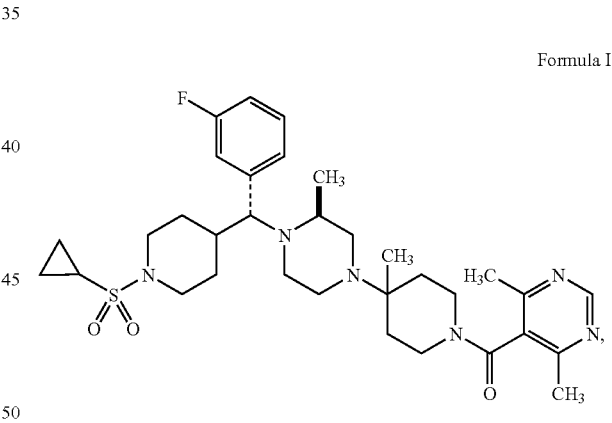

Formula I wherein said mixture comprises one rotamer of the salt in a mole percent ratio of greater than 55:45 in comparison with other rotamers present in said mixture, and wherein said salt is prepared by a process comprising reacting said substituted piperazinyl compound with an acid which is benzenesulfonic acid, camphor sulfonic acid, glutaric acid, 2-ketoglutaric acid, nicotinic acid, or benzoic acid in admixture with a solvent which is water, a ketone, an ether, an ester, an alcohol, a nitrile, a hydrocarbon or mixtures thereof.

2. The mixture of claim 1, wherein said mixture is provided by a process using a solvent which is ethyl acetate, isopropyl acetate, tetrahydrofuran acetone, ethanol, isopropanol, toluene, acetonitrile, a hydrocarbon or mixtures of two or more thereof.

3. The mixture of rotamers of claim 1 wherein said salt is a benzenesulfonate salt of a substituted piperazinyl compound of the formula:

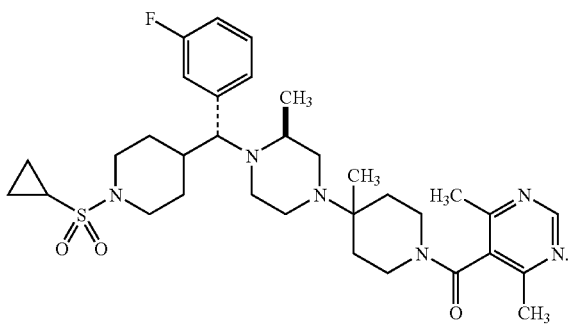

4. The mixture of rotamers of claim 1 wherein said salt is a D-10-camphorsulfonate salt of a substituted piperazinyl compound of the formula:

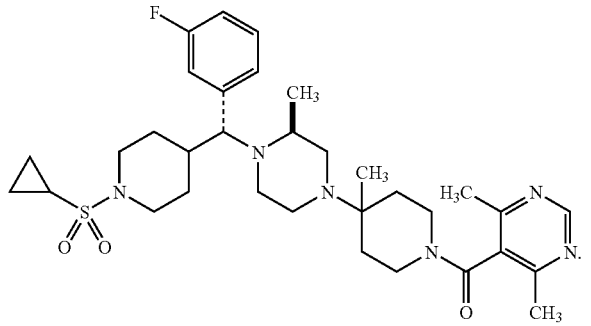

5. The mixture of retainers of claim 1 wherein said salt is a glutarate salt of a substituted piperazinyl compound of the formula:

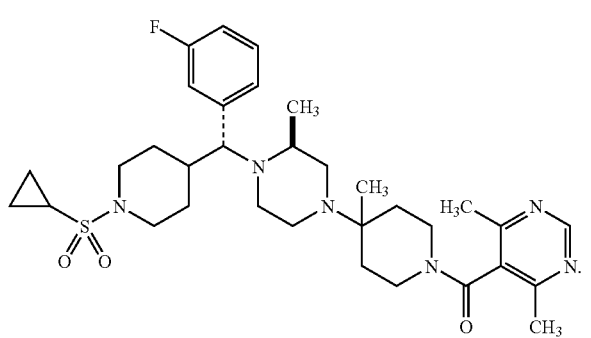

6. The mixture of rotamers of claim 1 wherein said salt is a 2-ketoglutarate salt of a substituted piperazinyl compound of the formula:

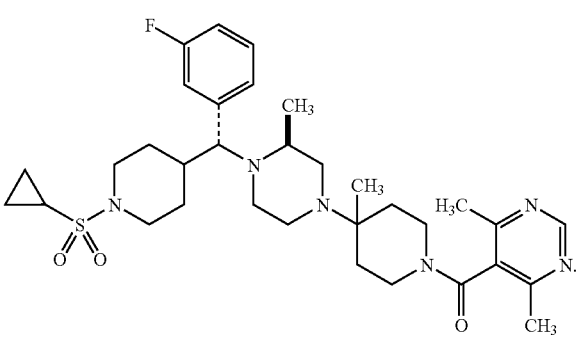

7. The mixture of retainers of claim 1 wherein said salt is a nicotinate salt of a substituted piperazinyl compound of the formula:

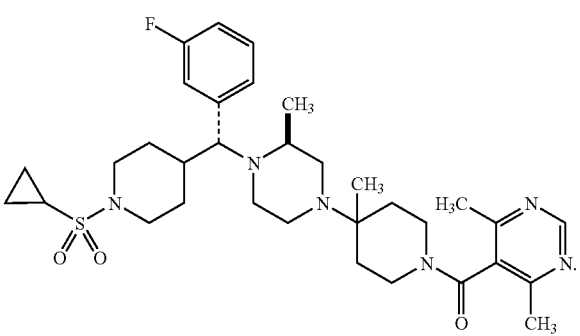

8. The mixture of retainers of claim 1 wherein said salt is a benzoate salt of a substituted piperazinyl compound of the formula:

9. A process for selectively crystallizing a rotamer of a salt of a compound of Formula 1:
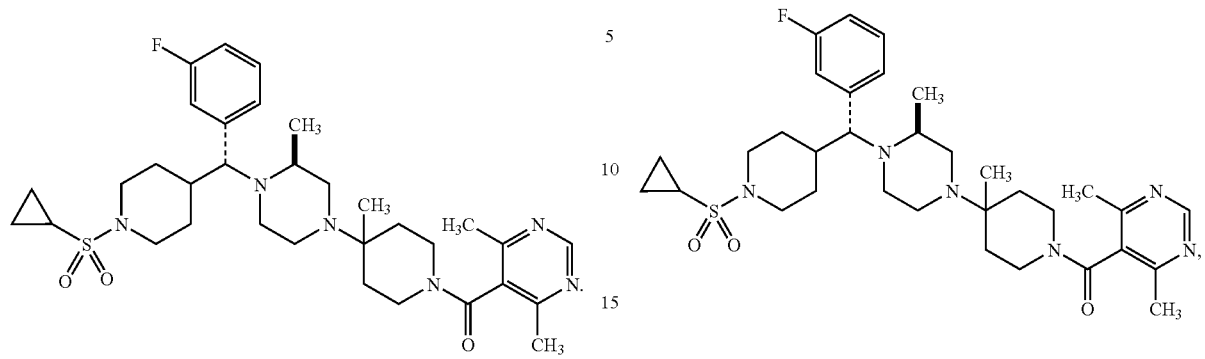
said process comprising reacting said compound of Formula 1 with an acid which is benzoic acid, benzenesulfonic acid, camphor sulfonic acid, nicotinic acid, glutaric acid or 2-ketoglutaric acid, in admixture with a solvent.
* * * * *

UNITED STATES PATENT AND TRADEMARK OFFICE
CERTIFICATE OF CORRECTION

PATENT NO. : 7,521,452 B2  Page 1 of 1
APPLICATION NO. : 11/326155
DATED : April 21, 2009
INVENTOR(S) : Wenxue Wu et al.

It is certified that error appears in the above-identified patent and that said Letters Patent is hereby corrected as shown below:

Claim 5, col. 17, line 48, please correct "retainers" to:

-- rotamers --

Claim 7, col. 18, line 33, please correct "retainers" to:

-- rotamers --

Claim 8, col. 18, line 65, please correct "retainers" to:

-- rotamers --

Signed and Sealed this

Tenth Day of November, 2009

David J. Kappos
*Director of the United States Patent and Trademark Office*